(12) United States Patent
Rowley et al.

(10) Patent No.: US 7,205,261 B2
(45) Date of Patent: Apr. 17, 2007

(54) USE OF CERTAIN N-ACYLETHANOLAMINES TO ACHIEVE ETHYLENE- AND CYTOKININ-LIKE EFFECTS IN PLANTS AND FUNGI

(75) Inventors: Keith Rowley, Madison, WI (US); Sang Won Jeong, Madison, WI (US); Keith Cowan, Stockholm (SE)

(73) Assignee: Nutra-Park, Inc., Middleton, WI (US)

( * ) Notice: Subject to any disclaimer, the term of this patent is extended or adjusted under 35 U.S.C. 154(b) by 377 days.

(21) Appl. No.: 10/636,109

(22) Filed: Aug. 7, 2003

(65) Prior Publication Data

US 2004/0082478 A1    Apr. 29, 2004

Related U.S. Application Data

(60) Provisional application No. 60/440,190, filed on Jan. 15, 2003, provisional application No. 60/402,461, filed on Aug. 9, 2002.

(51) Int. Cl.
*A01N 37/20* (2006.01)
*A01P 21/00* (2006.01)
*A23B 7/154* (2006.01)

(52) U.S. Cl. ............... 504/334; 504/339; 514/617; 514/625; 514/645; 426/442

(58) Field of Classification Search ........... 504/334, 504/339; 514/617, 625, 645; 426/442
See application file for complete search history.

(56) References Cited

U.S. PATENT DOCUMENTS 5,129,950 A    7/1992   Ghyczy et al.

6,200,586 B1 *   3/2001   Lambie et al. ............... 424/417

FOREIGN PATENT DOCUMENTS

| GB | 2 282 327 | 4/1995 |
|---|---|---|
| WO | WO 99/23889 | 5/1999 |
| WO | WO 01/30143 A2 | 5/2001 |

OTHER PUBLICATIONS

Austin-Brown, et al.; Plant Physiology, Aug. 2002, vol. 129, pp. 1892-1898.
Chapman; Trends in Plant Science, Nov. 1998, vol. 3, pp. 419-426.
Chapman, et al.; Plant Physiol. (1998) 116: 1163-1168.
Chapman; Chemistry and Physics of Lipids 108 (2000) 221-230.
Hoang, et al.; Plant Physiology, Apr. 2002, vol. 128, pp. 1417-1427.
Mason; Aug. 20, 2001; Study of plant enzymes gives cut flowers new power; http://www.kmsb.com/homegarden/house/flowers.448955.html.
Munnik; Trends in Plant Science, vol. 6, No. 5, pp. 227-233, May 2001.
Petersen; Characterization and Partial Purification of N-Acylethanolamine Phospholipid-Hydrolyzing Phospholipase; Abstract; http://www.dfh.dk/phd/defences/gittepedersen.html.
Tripathy, et al.; Plant Physiology, Dec. 1999, vol. 121, pp. 1299-1308.
N-Acylethanolamine Signaling in Plants; http://www.biol.unt.edu/~chapman/template_Jane.html.

\* cited by examiner

*Primary Examiner*—S. Mark Clardy
(74) *Attorney, Agent, or Firm*—Quarles & Brady, LLP

(57) ABSTRACT

N-acylethanolamines (NAEs) that can deliver an ethylene- or cytokinin-like effect to a plant, plant part or fungus are disclosed. Also disclosed are methods of using the NAEs.

8 Claims, 6 Drawing Sheets

Control 20 mg/L Kinetin

USE OF CERTAIN N-ACYLETHANOLAMINES TO ACHIEVE ETHYLENE- AND CYTOKININ-LIKE EFFECTS IN PLANTS AND FUNGI

CROSS-REFERENCE TO RELATED APPLICATIONS

This application claims priority to U.S. provisional application Ser. No. 60/402,461, filed on Aug. 9, 2002, and U.S. provisional application Ser. No. 60/440,190, filed on Jan. 15, 2003.

STATEMENT REGARDING FEDERALLY SPONSORED RESEARCH OR DEVELOPMENT

Not applicable

BACKGROUND OF THE INVENTION

Since many plants and plant parts are of economic importance to people, people have learned to manipulate the life cycle of plants for their own purposes. Various chemical and biological agents are used on commercially grown fruits and vegetables to control the timing of fruit and vegetable ripening. Some agents are used to synchronize the ripening of fruits and vegetables to assist in efficient harvesting of fruits and vegetables from the field. Other agents are used to inhibit fruit drop so that fruits remain on the plant or tree until the appropriate ripening time period. Another purpose of fruit and vegetable ripening agents is to enhance color development in a fruit or vegetable so that the fruit or vegetable has a better and more uniform color as expected by retail consumers of the fruit or vegetable. In the United States, it is current practice for many types of fruits and vegetables to be treated with one or more such agents during the growing season and after harvest. However, many of these ripening agents also cause fruits and vegetables to soften leading to a very poor storage and shelf life. An example of a ripening agent is ethephon, sold in many commercial formulations, which is used to accelerate the ripening of certain fruits, even though it simultaneously negatively impacts fruit quality. In addition, many of these agents are synthetic and have toxicological and environmental concerns such that they are not viewed favorably by fruit and vegetable consumers.

Another class of agents that is of great interest to the plant industry is the class that has senescence retardation activity. These agents can prolong the shelf life of fruits, vegetables and cut flowers. However, the timing of application of such agents can be critical to avoid unripened or immature fruit. An example of an agent used to prolong shelf life is 1-methyl cyclopropene or MCP, which is commonly used to prolong the shelf life of picked fruit. Similar to the ripening agents, many of the senescence retardation agents have toxicological and environmental concerns.

Certain members of the N-acylethanolamine (NAE) family are other examples of agents that have senescence retardation activities. Chapman, K. D. et al. (WO01/30143 (2001)) demonstrated that certain NAEs could be used to prolong the shelf life of cut flowers. Dr. Chapman speculated that in consistence with the senescence retardation activity, these NAEs may also possess the ability to slow down the ripening process in plant parts (http://www.kmsb.com/homegarden/house/flowers.448955.html), as do other senescence retardation agents.

In the recent years, naturally derived materials with good ripening and senescence retardation effects have been identified. For example, certain phospholipids (such as lysophosphatidylethanolamine (LPE) and lysophosphatidylinositol (LPI)) have been shown to accelerate fruit ripening, enhance fruit stability during storage, and increase the shelf life of plant parts by retarding senescence of plant tissues. Farag, K. M. et al., Physiol. Plant, 87:515–524 (1993); Farag, K. M. et al., HortTech., 3:62–65 (1993); Kaur, N., et al., HortScience, 32:888–890 (1997); Ryu, S. B., et al., Proc. Natl. Acad. Sci. U.S.A., 94:12717–12721 (1997); U.S. Pat. Nos. 5,126,155 and 5,110,341; and WO 99/23889. More agents like these naturally derived materials that have both ripening enhancement and senescence retardation effects are desirable in the plant industry.

BRIEF SUMMARY OF THE INVENTION

In one aspect, the present invention relates a method of delivering an ethylene-like effect to a whole plant or plant part by treating the plant or plant part with one or more NAEs having a structure of $RCONHCH_2CH_2OH$, wherein R is hydrogen, or a straight, branched, cyclic or polycyclic, saturated or unsaturated $C_1$–$C_{22}$ alkyl group. The ethylene-like effects that can be delivered by the NAEs include but are not limited to enhancement of ripening or maturation of a plant part, enhancement of color change of a fruit or leaf, reduction in size of a plant or plant part, and promotion of cotton boll opening.

In another aspect, the present invention relates a method of delivering a cytokininlike effect to a whole plant, plant part or fungus by treating the plant, plant part or fungus with one or more NAEs having a structure of $RCONHCH_2CH_2OH$, wherein R is hydrogen, or a straight, branched, cyclic or polycyclic, saturated or unsaturated $C_1$–$C_{22}$ alkyl group. The cytokinin-like effects that can be delivered by the NAEs include but are not limited to maintaining or enhancement of plant vigor, enhancement of the number or size of the plant, plant part or fungus, chlorophyll retention, enhancement of storage stability of mushrooms, and enhancement of production a plant part on a growing plant.

It is an advantage of the present invention that the NAEs are easy to apply to a plant part so that the ripening or maturation enhancement of the plant part can be combined with other treatments of the plant part to save on cost.

Other objects, advantages and features of the present invention will become apparent from the following specification.

DETAILED DESCRIPTION OF THE INVENTION

Figure 1:
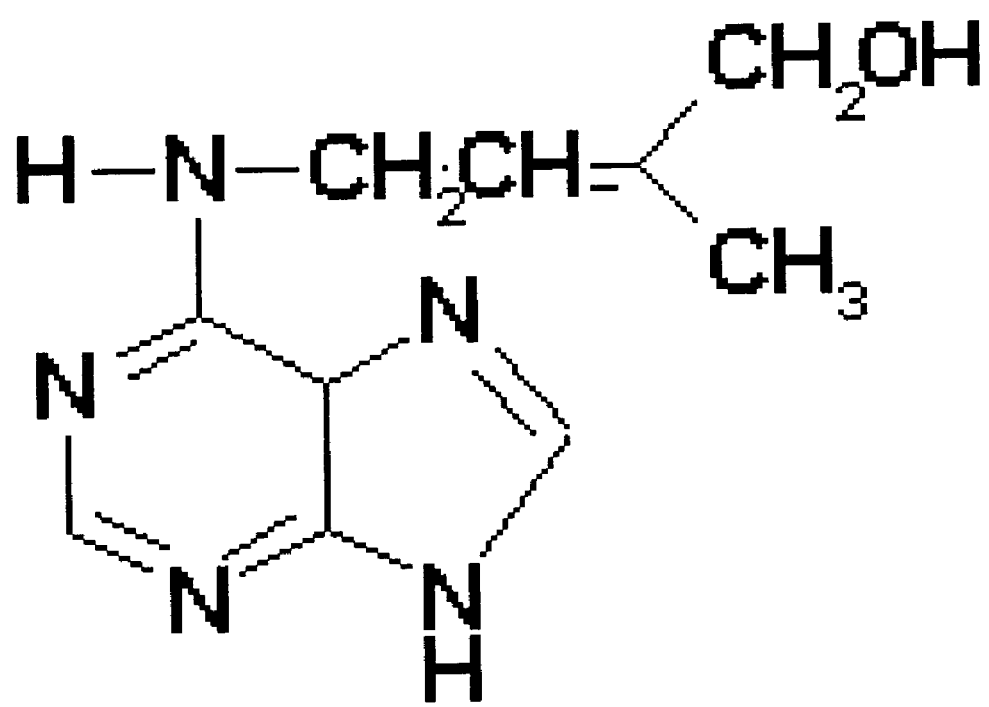
FIG. 1 shows the chemical structure of zeatin.
Figure 2:
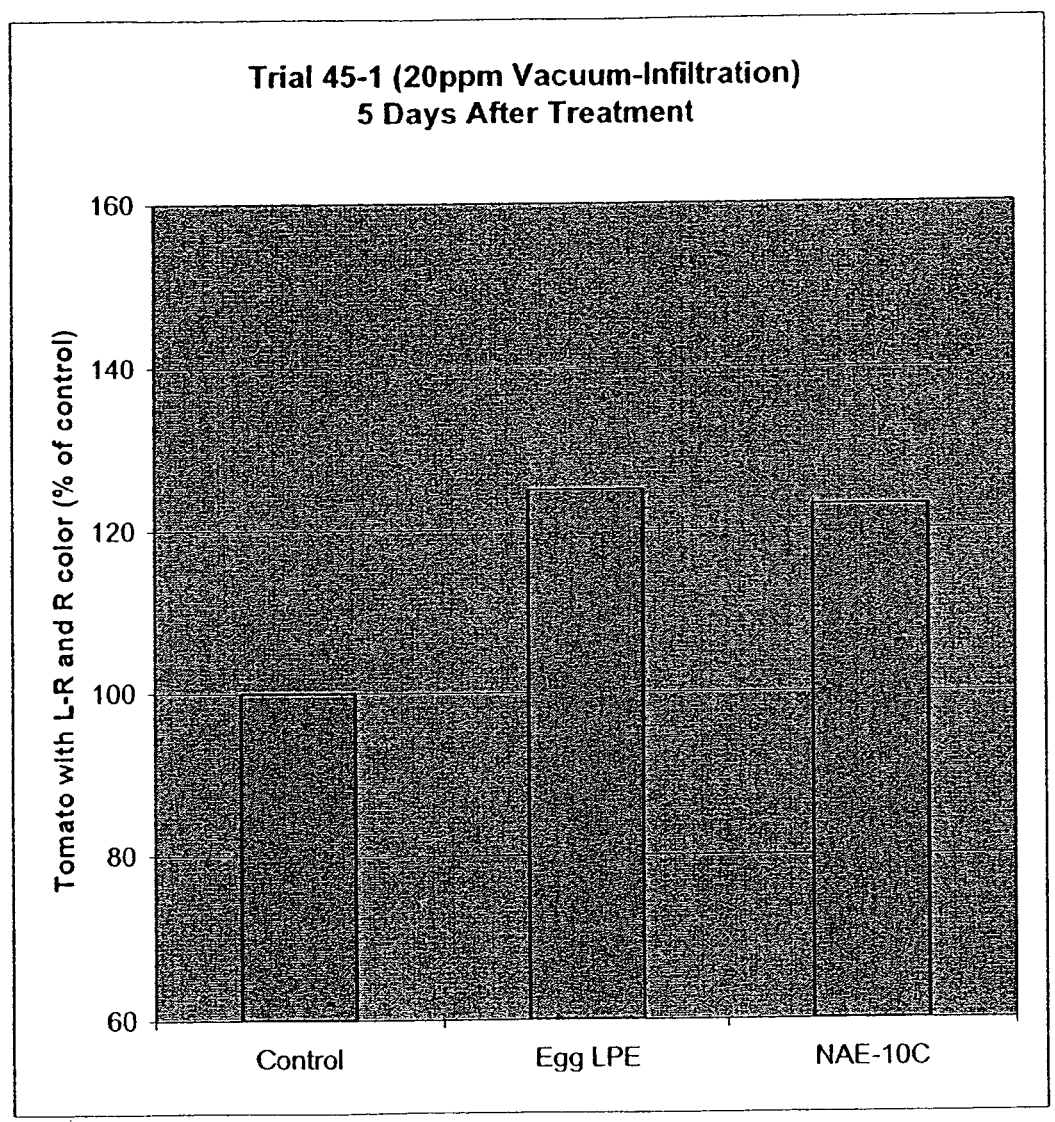
FIGS. 2–5 show the effect of NAE-10:0 (shown as NAE-10C) and NAE-14:0 (shown as NAE-14C) on the ripening of harvested tomatoes. As indicated in the figures, the tomatoes were either sprayed with 500 ppm (=500 mg/l) NAE-10:0 or NAE-14:0, or vacuum infiltrated with 20 ppm (=20 mg/l) NAE-10:0 or NAE-14:0.
Figure 3:
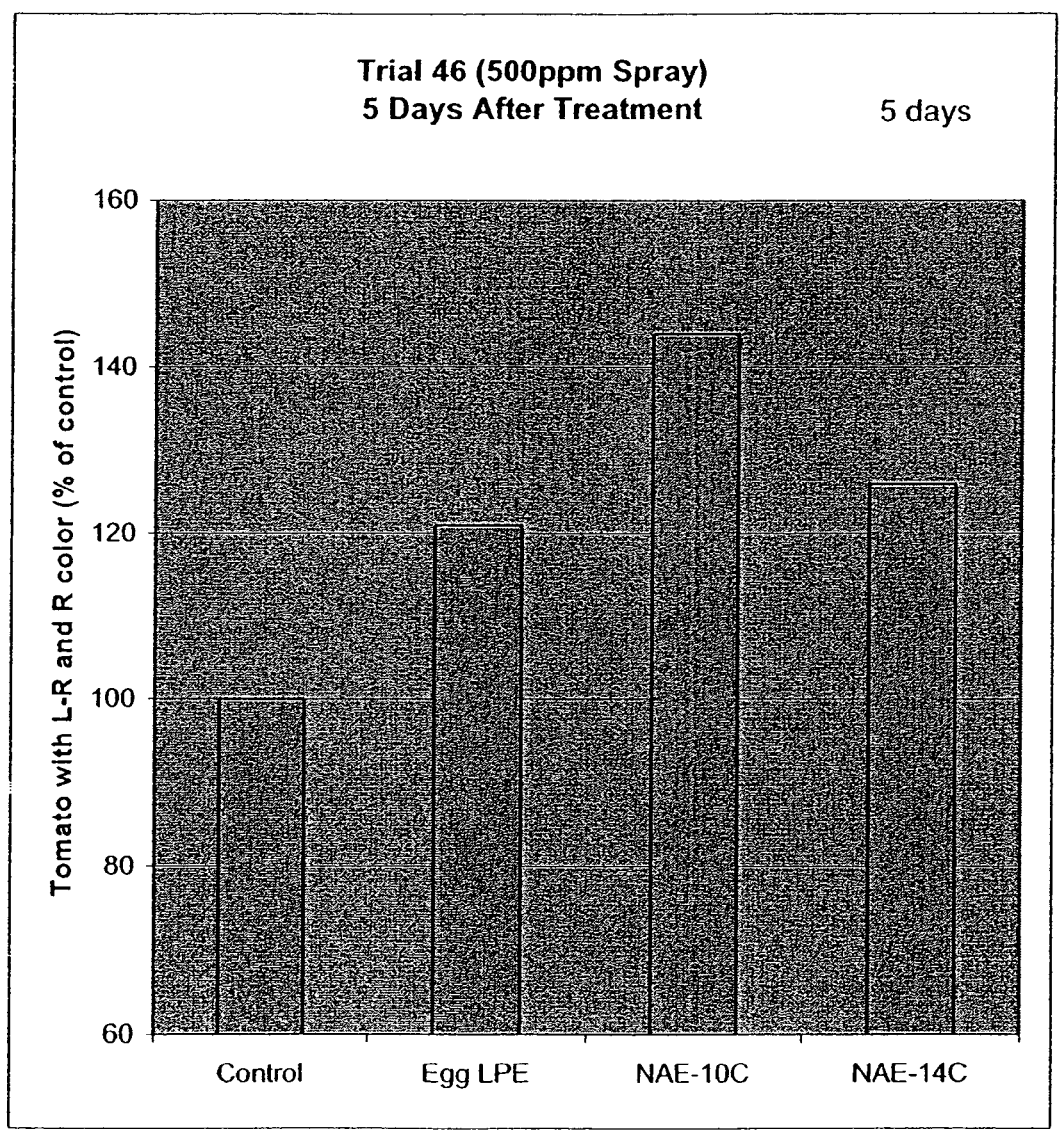
Figure 4:
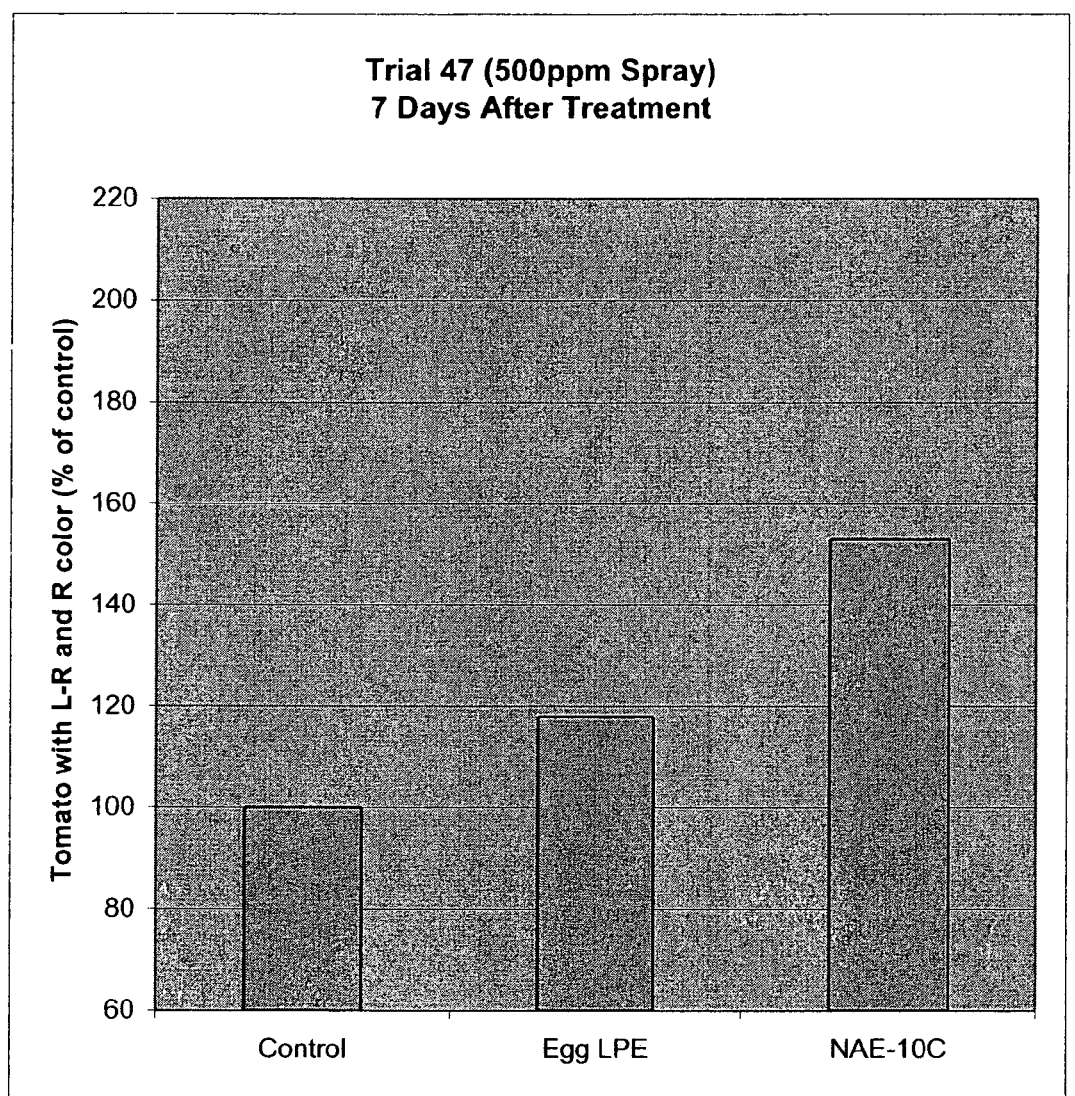
Figure 5:
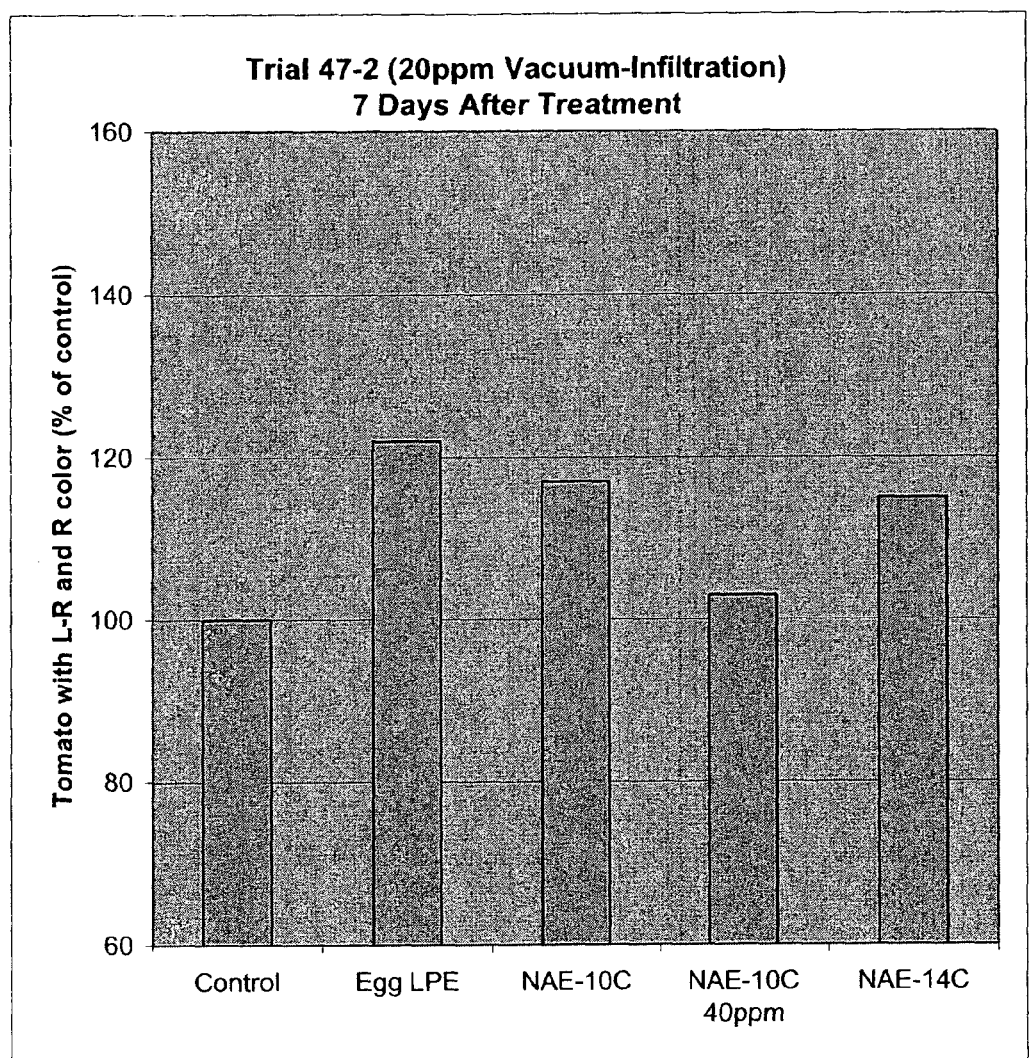

It is disclosed here that a limited number of N-acylethanolamines (NAEs) can deliver hormonal effects on plant growth that result in changes in the life cycle of growing plants, plant parts and fungi. In particular, these NAEs can mimic the effects of the plant hormone ethylene, cytokinins or both. This has been demonstrated with several particular NAEs from the limited NAE group defined herein below for several ethylene and cytokinin effects. It is well known in the art that ethylene and cytokinins have many different effects on plants and plant parts and the exact effect depends on the particular hormone and the plant species. What is important here is the determination that only a limited number of NAEs defined herein below have ethylene- and cytokinin-like activities. The exact activity of a particular NAE from the limited NAE group for a particular effect of ethylene or cytokinin, if not already demonstrated in the examples below, can be easily determined by a skilled artisan through routine experimentation.

It is disclosed here that the NAEs that can deliver the hormonal effects of ethylene, cytokinins or both are limited to those that have the structure of $RCONHCH_2CH_2OH$, wherein R is hydrogen, or a straight, branched, cyclic or polycyclic (e.g., aromatic), saturated or unsaturated $C_1$–$C_{22}$ alkyl group. These NAEs are hereinafter referred to as $C_0$–$C_{22}$ NAEs for the purpose of the present invention. A shorthand notation of NAE-X:Y($\Delta$n) is used for an NAE having a straight alkyl R group to indicate that the acyl chain length of the NAE is X, the number of double bonds in the NAE is Y, and the double bond(s) is(are) positioned at the nth carbon of the acyl chain if there is(are) double bond(s) in the acyl chain. The NAEs disclosed here can be used individually or in combination with one another. As examples, NAE-1, NAE-2, NAE-4:0, NAE-6:0, NAE-8:0, NAE-10:0, NAE-18:1($\Delta$1) have been shown to have ethylene-like activities and NAE-4:0, NAE-10:0, NAE-12:0, NAE-14:0, NAE-16:0, NAE-18:1($\Delta$9) have been shown to have cytokinin-like activities in the examples below.

Ethylene is a plant hormone and is the only member of its class. All higher plants produce ethylene. The ethylene production varies with the type of tissue, the plant species and the stage of development (Salisbury, F B and Ross, C W (1992) *Plant Physiology*, Belmont, Calif.: Wadsworth. pp. 357–407, 531–548; and McKeon, TA, et al. (1995) Biosynthesis and metabolism of ethylene, In P J Davies (ed) *Plant Hormones: Physiology, Biochemistry and Molecular Biology*, Dordrecht: Kluwer. pp. 118–139, both of which are incorporated by reference in their entirety). Ethylene is known to be able to stimulate the maturation or ripening of a plant or plant part. For example, the production of ethylene has been manipulated to modulate fruit ripening and color change. Ethylene can also be used to reduce the size of a plant or plant organ. Ethylene is also known to stimulate leaf and fruit abscission, flower opening, Bromeliad flower induction, flower and leaf senescence, shoot and root growth and differentiation, adventitious root formation, release from dormancy, and femalesness in dioecious flowers (Davies P J (1995) *Plant Hormones: Physiology, Biochemistry and Molecular Biology*, Dordrecht: Kluwer Academic; Mauseth, J D (1991) *Botany: An Introduction to Plant Biology*, Philadelphia, Saunders. pp. 348–415; Raven, PH et al. (1992) *Biology of Plants*, New York: Worth. pp. 545–572; and Salisbury, FB and Ross, C W (1992) *Plant Physiology*, Belmont, Calif.: Wadsworth. pp. 357–407, 531–548, all of which are incorporated by references in their entirety). For field crops or parts in particular, such as cotton bolls, ethylene can promote opening.

The examples below demonstrate that $C_0$–$C_{22}$ NAEs have ethylene-like activities. It is expected that all the effects of ethylene such as those described above can be mimicked by this limited group of NAEs. For example, one can use a $C_0$–$C_{22}$ NAE to enhance the ripening or maturation of a plant or plant part, such as ripening or maturation of a fruit or vegetable, to enhance the color change of a fruit or vegetable, to reduce the size of a plant or plant part, such as pot size or fruit size, and to promote cotton boll opening. Regardless of whether a plant part (e.g., a fruit, a flower, a seed, a leaf, a root, or a stem) is still on a growing plant or has been harvested from the plant, treating the whole plant or the plant part with one or more of the $C_0$–$C_{22}$ NAEs can enhance the ripening or maturation of that plant part. For a particular application, the effect of a particular NAE from the $C_0$–$C_{22}$ NAE group on a particular plant species or an organ or tissue thereof, if not already demonstrated in particular in the examples below, can be readily determined by a skilled artisan through routine experimentation. For example, a plant part must typically reach a certain level of maturity in order for the $C_0$–$C_{22}$ NAEs to be effective in enhancing ripening and maturity. The examples below demonstrated that for harvested tomatoes, the tomatoes must reach mature green 4 stage in order for the NAEs to have optimal effect. The less mature the tomatoes are from green 4 stage, the less effective the NAEs are. A skilled artisan can readily determine through routine experimentation the mature stage needed for other plant parts and fruits of other plant species. Since the NAEs are known to have anti-senescence activities as well, treating a plant or plant part with an NAE for enhancing ripening or maturation has the advantage of not shortening the storage or shelf life of the plant part.

Cytokinins belong to a class of plant hormones that can promote cytokinesis (cell division). There are over 200 natural and synthetic cytokinins. Structurally, cytokinins resemble adenine and are produced in plants by biochemical modification of adenine (McGaw, BA (1995) *Cytokinin biosynthesis and metabolism*, In PJ Davies (ed) *Plant Hormones: Physiology, Biochemistry and Molecular Biology*, Dordrecht: Kluwer. pp.98–117, incorporated by reference in its entirety; and Salisbury, FB and Ross, CW (1992) *Plant Physiology*, Belmont, Calif.: Wadsworth. pp. 357–407, 531–548). Cytokinins have been found in almost all higher plants as well as mosses, fungi, bacteria and also in tRNA of many prokaryotes and eukaryotes. The first identified cytokinin, kinetin, is a natural compound that is not made in plants. Although a natural compound, kinetin is sometimes referred to as a "synthetic" cytokinin by some people to indicate its non-plant origin. The most commonly made cytokinin by plants is zeatin (FIG. 1), which was first isolated from corn (*Zea mays*).

In plants, cytokinin concentrations are highest in meristematic regions and areas of continuous growth such as roots, young leaves, developing fruits, and seeds (Arteca, R (1996) *Plant Growth Substances: Principles and Applications*, New York: Chapman & Hall; Mauseth, JD (1991) *Botany: An Introduction to Plant Biology*, Philadelphia, Saunders. pp. 348–415; Raven, PH et al. (1992) *Biology of Plants*, New York: Worth. pp. 545–572; Salisbury, FB and Ross, CW (1992) *Plant Physiology*, Belmont, Calif.: Wadsworth. pp. 357–407, 531–548). This is consistent with the cytokinesis activity of the cytokinins. Besides promoting cytokinesis, depending on the particular cytokinin and plant species, some other physiological effects of cytokinesis include stimulation of morphogenesis (shoot initiation/bud formation), stimulation of the growth of lateral buds (release of apical dominance), stimulation of cell enlargement resulting in larger plant or organ size (e.g., larger pot size, leaf size and fruit size), stimulation of stomatal opening and promotion of the conversion of etioplasts into chloroplasts by stimulating chlorophyll synthesis.

The cytokinin-like activities of $C_0$–$C_{22}$ NAEs are demonstrated in the examples below with an art-recognized cytokinin efficacy assay, the radish cotyledon bioassay. It is expected that $C_0$–$C_{22}$ NAEs can be used to mimic all the effects of cytokinins such as those described above. For example, a $C_0$–$C_{22}$ NAEs can be used to maintain or enhance plant vigor, to enhance the number or size of flowers and fruits on a growing plant, to maintain lawn or grass through green pigment retention, and to enhance storage stability of fungi (e.g., mushrooms), organisms often thought of as not being plant. To enhance the storage stability of harvested mushrooms, the NAE can be applied at either the pre- or post-harvest stage. For a particular application, the effect of a particular NAE from the $C_0$–$C_{22}$ NAE group on a particular plant species or an organ or tissue thereof, if not already demonstrated in particular in the examples below, can be readily determined by a skilled artisan through routine experimentation.

The ethylene- or cytokinin-like activities of $C_0$–$C_{22}$ NAEs described above are not limited to any particular plant, plant part or fungus. Treatment conditions such as treatment time, treatment temperature and the amount of NAE used for a particular application may vary depending on variables such as the specific NAE used, the particular plant part treated and the purpose of the treatment. Appropriate treatment conditions for any particular application can be readily determined by a skilled artisan.

Any suitable method for applying an NAE to a target plant, plant part or fungus can be used in the present invention. Preferably, an NAE is provided in a solution for applying onto the target plant, plant part or fungus. Suitable solvents for making NAE solutions include but are not limited to water and organic solvents such as alcohol solvents (e.g., isopropanol). Examples of NAE concentrations that can be used include those from about 1 mg/l to about 2000 mg/l, from about 10 mg/l to about 1000 mg/l and from about 20 mg/l to about 500 mg/l. The term "about" is used in the specification and claims to cover concentrations that slightly deviate from the recited concentration but retain the essential function of the recited concentration. For treating a target plant, plant part and mushrooms, the plant, plant part and mushrooms can be sprayed with, dipped into or vacuum infiltrated with an NAE solution. Examples of NAE formulations suitable for plant, plant part and mushroom application and application methods thereof are described in WO 01/30143, which is herein incorporated by reference in its entirety. Other NAE-related information is also disclosed in WO 01/30134.

An advantage of the present invention is that applying NAE to a target plant part does not require sophisticated formulation and apparatus and thus can be combined with other treatments to save on cost. Using harvested tomatoes as an example, these tomatoes usually go through post-harvest processing steps such as washing, rinsing and waxing before reaching to the retail shelf. NAE treatment can be combined with any of these post-harvest processing steps.

By way of example, but not limitation, examples of the present invention is described below.

EXAMPLE 1

Synthesis and Characterization of NAE

Synthesis of N-formyl-2-aminoethanol (NAE-1): A solution of ethanolamine (3.00 g, 49.12 mmol) and ethyl formate (100 ml) was refluxed overnight. After evaporation of ethyl formate in vacuo, the residue was purified by flash column chromatography, eluting with a gradient of dichloromethane/methanol (95:5) to dichloromethane/methanol (9:1) to give 3.46 g of an oily NAE-1 (79% yield): $R_f$=0.063 in dichloromethane/methanol (95:5); $^1$H NMR (CDCl$_3$) δ 8.21 (s, 1H), 6.31 (br, 1H), 3.75 (m, 2H), 3.67 (m, 2H), 2.93 (br, 1H); FT-IR (Table 1)

Synthesis of N-decanoyl-2-aminoethanol (NAE-10:0): A solution of ethanolamine (3.42 ml, 56.6 mmol) and triethylamine (5.51 ml, 39.5 mmol) in dry tetrahydrofuran (150 ml) was cooled in ice bath and decanoyl chloride (5.44 ml, 26.3 mmol) in tetrahydrofuran (50 ml) was added dropwise. The reaction mixture was stirred at room temperature overnight and filtered. The filtered solution was concentrated in vacuo. The residue was diluted with ethyl acetate (300 ml) and washed with 0.1% HCl (50 ml×3), saturated NaHCO$_3$ (50 ml×3), brine (50 ml), and water (50 ml). The organic solution was dried over MgSO$_4$ and solvent was removed on a rotovap. The crude product was purified by flash column chromatography, eluting with a gradient of dichloromethane/methanol (95:5) to dichloromethane/methanol (9:1) to give 5.57 g of a white solid NAE-10:0 (99% yield): $R_f$=0.35 in dichloromethane/methanol (95:5); $^1$H NMR (CDCl$_3$) δ 6.11 (br, 1H), 3.72 (m, 2H), 3.42 (m, 2H), 3.08 (br, 1H), 2.20 (t, J=7.9 Hz, 2H), 1.64 (m, 2H), 1.26–1.29 (m, 12H), 0.88 (t, J=6.8 Hz, 3H); FT-IR (Table 1).

The N-acyl-2-aminoethanol derivatives (NAE-2, NAE-4:0, NAE-6:0, NAE-8:0, NAE-12:0, NAE-14:0, NAE-16:0, NAE-18:0, NAE-18:1(Δ9), NAE-EH, NAE-Bz) were prepared by following the abovementioned procedure, using the corresponding acyl chloride. The analytical data are summarized in Table 1.

Synthesis of N-(9,10-dihydroxyoctadecanoyl)-2-aminoethanol (NAE-18DH): A solution of 9,10-dihydroxyoctanoic acid (1,000 mg, 3.16 mmol), prepared according to a literature procedure (Organic Synthesis, Col. Vol 4, 317), and N-hydroxysuccinimide (727.4 mg, 6.32 mmol) in N,N-dimethylformamide (DMF) was cooled in ice bath. 1-(3-(Dimethylamino)propyl)-3-ethylcarbodiimide hydrochloride (EDCI) was added in one portion. The reaction mixture was stirred at room temperature for 5 h. After addition of ethanolamine (0.763 ml, 12.64 mmol) and triethylamine (TEA) (1.761 ml, 12.64 mmol), the reaction mixture was stirred overnight. After aqueous workup, the crude compound was precipitated from ethyl acetate twice to give 0.49 g of white solid (43% yield): $R_f$=0.15 in dichloromethane/methanol (95:5); $^1$H NMR (CDCl$_3$+CD$_3$OD) δ 3.63 (m, 2H), 3.31–3.37 (m, 4H), 2.21 (t, J=7.5 Hz, 2H), 1.63 (m, 2H), 1.50–1.24 (m, 24H), 0.89 (t, J=6.6 Hz, 3H); FT-IR (Table 1).

TABLE 1

Characterization of N-acylethanolamine

| Code | | Yield (%) | $R_f$ dichloromethane/ methanol (95:5) | FT-IR (neat) cm$^{-1}$ |
|---|---|---|---|---|
| NAE-1 | N-Formyl-2-aminoethanol | 79 | 0.063 | 3284, 1649, 1531, 1381, 1243, 1061 |
| NAE-2 | N-Acetyl-2-aminoethanol | 76 | 0.16 | 3282, 1630, 1550, 1373, 1291, 1060 |
| NAE-4:0 | N-Butyroyl-2-aminoethanol | 46 | 0.24 | 3289, 1629, 1547, 1213, 1061 |
| NAE-6:0 | N-Hexanoly-2-aminoethanol | 99 | 0.25 | 3286, 1639, 1555, 1215, 1034 |
| NAE-8:0 | N-Octanoyl-2-aminoethanol | 97 | 0.30 | 3291, 1639, 1555, 1211, 1243, 1034 |
| NAE-10:0 | N-Decanoyl-2-aminoethanol | 99 | 0.35 | 3292, 1640, 1556, 1038 |
| NAE-12:0 | N-Dodecanoyl-2-aminoethanol | 91 | 0.35 | 3287, 1634, 1552, 1386, 1276, 1048 |
| NAE-14:0 | N-Tetradecanoyl-2-aminoethanol | 39 | 0.35 | 3293, 1640, 1555, 1039 |
| NAE-16:0 | N-Hexadecanoyl-2-aminoethanol | 23 | 0.35 | 3289, 1635, 1553, 1056 |
| NAE-18:0 | N-Octadecanoyl-2-aminoethanol | 12 | 0.35 | 3296, 1641, 1557, 1040 |
| NAE-18:1(Δ9) | N-Oleoyl-2-aminoethanol | 79 | 0.36 | 3291, 1642, 1560, 1058, 1035 |
| NAE-18DH | N-(9,10-Dihydroxyoctadecanoyl)-2-aminoethanol | 43 | 0.15 | 3292, 1644, 1555, 1464, 1058, 1037 |
| NAE-EH | N-(2-Ethylhexanoyl)-2-aminoethanol | 74 | 0.34 | 3278, 1642, 1553, 1033 |
| NAE-Bz | N-Benzoyl-2-aminoethanol | 55 | 0.35 | 3302, 1634, 1536, 1291, 1056, 1036 |

EXAMPLE 2

Tomato bioassay: NAE solutions containing 20 ppm or 500 ppm of NAE were used to treat harvested tomatoes as described below. The solutions were prepared by dispersing a solid NAE compound in water through sonication.

Egg LPE was purchased from Avanti Polar Lipids (Alabaster, Ala.). Egg LPE solutions containing 20 ppm or 500 ppm LPE were used as positive controls in the assays described below. The solutions were prepared by dispersing LPE into water through sonication or aggressive agitation.

The tomatoes used in this study were tomato variety FL47 (cultivar), 6×6 mature green tomatoes of good quality MG3–4 (Breaker stage: no apparent external change from green to pink). The tomatoes were purchased from West Coast Tomato (Palmetto, Fla.) and Dimare Tomato (Homestead, Fla.).

The system used for classifying tomato mature stages is as the follows: Green (Stage 1)—"Green" means that the surface of the tomato is completely green in color. The shade of green may vary from light to dark. Breakers (Stage 2)—"Breakers" means there is a definite "break" in color from green, to tannish-yellow, pink or red on not more than 10% of the surface. Turning (Stage 3)—"Turning" means that more than 10% but not more than 30% of the surface, in the aggregate, shows a definite change in color from green to tannish-yellow, pink, red or a combination thereof. Pink (Stage 4)—"Pink" means that more than 30% but not more than 60% of the surface, in the aggregate, shows pink or red in color. Light Red (L-R) (Stage 5)—"Light red" means that more than 60% of the surface, in the aggregate, shows pinkish-red or red, provided that not more than 90% of the surface is red. Red (R) (Stage 6)—"Red" means that more than 90% of the surface, in the aggregate, is red.

Mature Green (MG) Tomato stages are defined as follows: MG1-Fruit is completely green, hard, and when cut into sections, shows no signs of locular gel formation. Locules contain hard, white substance. MG2-Fruit is completely green, hard, and when sectioned shows some (10–40%) locular gel formation. Seeds are forming and are white. MG3-Fruit is completely green, firm, and when sectioned shows (50–90%) jocular gel formation. Seeds are fully formed and are turning from white to beige. MG4-Fruit are softening a little but still completely green on the outside. Inside locular gel is completely formed with hints of pink coloration in the columella tissue. Seeds are dark beige to light brown.

In spray application bioassays, the tomatoes were placed in 100° F. water for 90 seconds, after which the tomatoes were removed from water and placed stem scar up onto a sheet of plastic. An NAE solution or LPE solution was sprayed onto the tomatoes at 30 psi using a flat fan tip situated approximately 8 to 10 inches above the tomatoes. The tomatoes were air dried and placed on a sheet of white paper with stem scar down under consistent environmental conditions. Five to seven days later, the ripening of the tomatoes were determined by visual observation of the color of the tomatoes.

In vacuum infiltration bioassay, each tomato was placed on top of a vacuum bell jar platform with stem scar facing up. 0.5 ml of NAE solution or LPE solution was placed onto stem scar and the glass bell jar lid was lowered onto the jar platform. The vacuum was started and the air escaped from the interior of the tomato causing the NAE solution or the LPE solution on the stem scar to bubble. After a preset time period, the air inlet was opened slowly to release vacuum in the bell jar. The NAE solution or the LPE solution on the stem scar was pulled into the tomato to replace the evacuated air. The tomato was then removed from the bell jar and placed on a sheet of white paper with stem scar down under consistent environmental conditions. Five to seven days later, the ripening of the tomatoes were determined by visual observation of the color of the tomatoes.

Results

As shown in FIGS. 2–5, spraying tomatoes with 500 ppm NAE-10:0 or NAE-14:0, or vacuum infiltrating tomatoes with 20 ppm NAE-10:0 or NAE-14:0 led to a higher number of ripened tomatoes 5 to 7 days after the treatment when compared to the control group. As a positive control, treating tomatoes with egg LPE also led to a higher number of ripened tomatoes.

EXAMPLE 3

Radish cotyledon bioassay: This bioassay using *Raphanus sativus* L. cv. Cherry Belle cotyledons was developed by Letham, DS (*Physiologia Plantarum* 25, 391–396, 1971, incorporated by reference in its entirety) to evaluate the efficacy of cytokinin on cell enlargement. Success using this assay is not restricted to radish. Other species in which a cytokinin requirement for cotyledon expansion has been demonstrated include mustard, cucumber, and sunflower. In addition to their effect on cell division, cytokinin plays a major role in driving cell enlargement. Compounds in this class of phytohormone and with cytokinin activity also help maintain photosynthetic activity and productivity and abolish proteolytic activity. In cotyledon leaf systems, a requirement for cytokinin is critical and removal of the roots (i.e. the presumed source of cytokinin) renders the cotyledon leaves unable to expand. Exposure to cytokinin (0.02–22 μg/ml) results in a dramatic increase in fresh weight of cotyledons within 72 hours. This effect is not observed with either gibberellin or auxin and is usually delayed or inhibited by abscisic acid and the ethylene precursor, 1-aminocyclopropane-1-carboxylic acid (ACC). The increase in fresh weight does not occur concomitant with an increase in dry weight. Thus, the mode of action of cytokinin in this system appears to be similar to that of indole-3-acetic acid (IAA) in auxin-induced stem elongation, a process that depends on an increase in the mechanical extensibility of the cell wall. However, cytokinin antagonizes IAA-mediated cell elongation and appears to do so by promoting ethylene production. Furthermore, cytokinin-induced cell expansion is not usually accompanied by proton ($H^+$) extrusion and no change in plasma membrane ATPase activity is evident.

Figure 6:
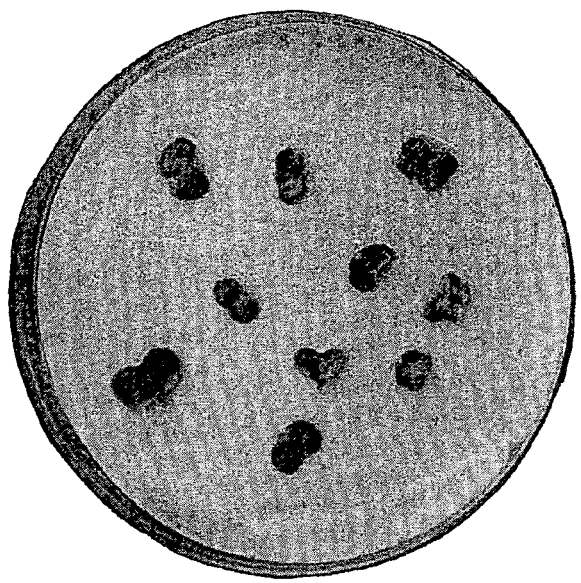
FIG. 6 shows the difference in cotyledon size in response to kinetin.
Figure 6:
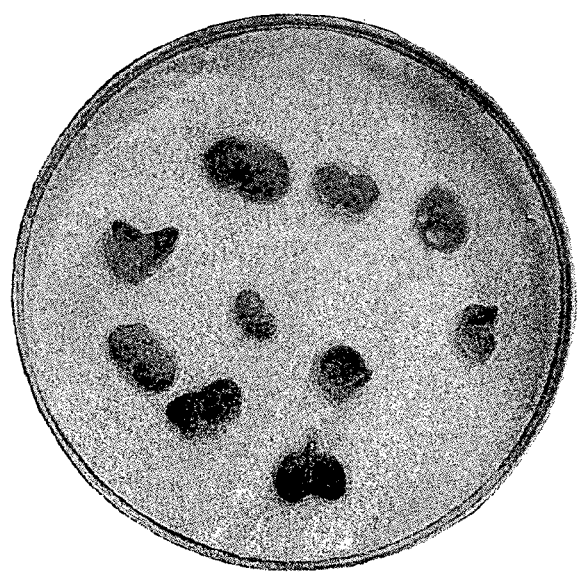

Seeds of *Raphanus sativus* L. cv. Cherry-Belle were germinated in darkness at 24° C. for 36 h in Petri dishes containing filter paper wetted with distilled water. The smaller of the two cotyledons was excised, the fresh weight determined, and 10 cotyledons placed adaxial side down on filter paper in Petri dishes containing 10 ml of $KPO_4$ buffer (2 mM, pH 6.0) and the compounds to be tested at 20 mg/l. Cotyledons were then incubated under continuous illumination for up to 72 h at 24° C. and the increase in fresh weight was determined. Chlorophyll content was determined after extraction of tissue into 80% ethanol (containing butylated hydroxytoluene (BHT) 10 mg/l) using the equations Chl a=$(13.95A_{663})-(6.88A_{647})$ and Chl b=$(24.96A_{652})-(7.32A_{663})$ as described by Lichtenthaler, HK, *Methods in Enzymology* 148: 350–382, 1987, incorporated by reference in its entirety. FIG. 6 illustrates the difference in cotyledon size in response to the cytokinin kinetin.

Results: From Table 2 (a 72 h incubation), NAE-1, NAE-2, NAE-6:0, NAE-8:0 and NAE-10:0 affected cotyledons similar to that of the ethylene precursor ACC. NAE-1 and NAE-6:0 had a more dramatic effect than other NAEs and they also significantly slowed cotyledon expansion. The NAEs tested also caused chlorophyll accumulation with NAE-2 and NAE-8:0 having a greater effect than other NAEs.

TABLE 2

Experiment 1: Effect of NAEs on expansion growth and chlorophyll accumulation of radish cotyledons. Ten cotyledons were incubated on filter discs wetted with 2 mM $KPO_4$ buffer (pH 6.0) containing either kinetin, ACC, or NAE (all 20 mg/l). Cotyledons were incubated under continuous illumination at 25° C. for 72 h and the change in fresh weight and chlorophyll content determined.

| Treatment | Change in fresh weight (mg) | % of control | Chlorophyll a + b (μg/cotyledon) | Chlorophyll a/b |
|---|---|---|---|---|
| Control | 14.00 ± 5.07 | 100 | 0.53 | 1.9 |
| Kinetin | 23.74 ± 7.92 | 169 | 0.55 | 1.2 |
| ACC | 5.54 ± 2.87 | 40 | 0.51 | 3.7 |
| NAE-1 | 7.61 ± 3.42 | 54 | 0.59 | 1.7 |
| NAE-2 | 12.52 ± 2.83 | 89 | 0.73 | 1.3 |
| NAE-6:0 | 8.04 ± 3.86 | 57 | 0.65 | 1.6 |
| NAE-8:0 | 13.32 ± 6.40 | 95 | 0.75 | 1.5 |
| NAE-10:0 | 10.34 ± 3.28 | 74 | 0.61 | 1.5 |

From Table 3 (a 48 h incubation), NAE-10:0 and NAE-16:0 showed cytokinin-like activity with respect to expansion growth whereas NAE-2, NAE-4:0, NAE-6:0, and NAE-18:1(Δ9) showed ethylene-like activity. NAE-10:0 and NAE-16:0 increased chlorophyll per cotyledon but decreased chlorophyll content per unit mass. NAE-2 and NAE-18: 1 (Δ9) showed ethylene-like activity and slowed cotyledon expansion.

TABLE 3

Experiment 2: Effect of NAEs on expansion growth and chlorophyll accumulation of radish cotyledons. Ten cotyledons were incubated on filter discs wetted with 2 mM $KPO_4$ buffer (pH 6.0) containing kinetin, ACC or NAE (all 20 mg/l). Cotyledons were incubated under continuous illumination at 25° C. for 48 h and the change in fresh weight and chlorophyll content determined.

| Treatment | Change in fresh weight (mg) | % of control | Chlorophyll (μg/cotyledon) a + b | Chlorophyll (mg/g FW) a + b | Chlorophyll a/b |
|---|---|---|---|---|---|
| Control | 8.11 ± 1.32 | 100 | 20.41 | 1.69 | 1.3 |
| ACC | 4.25 ± 0.63 | 52 | 12.27 | 1.42 | 1.8 |
| Kinetin | 27.26 ± 2.88 | 336 | 25.78 | 0.81 | 1.8 |
| NAE-1 | 8.68 ± 1.70 | 107 | 21.19 | 1.62 | 2.0 |
| NAE-2 | 5.86 ± 1.36 | 72 | 19.88 | 1.94 | 2.0 |
| NAE-4:0 | 7.15 ± 1.16 | 88 | 23.49 | 2.00 | 1.9 |
| NAE-6:0 | 7.02 ± 0.98 | 87 | 19.80 | 1.73 | 2.0 |
| NAE-8:0 | 8.29 ± 0.72 | 102 | 22.27 | 1.75 | 1.8 |

TABLE 3-continued

Experiment 2: Effect of NAEs on expansion growth and chlorophyll accumulation of radish cotyledons. Ten cotyledons were incubated on filter discs wetted with 2 mM $KPO_4$ buffer (pH 6.0) containing kinetin, ACC or NAE (all 20 mg/l). Cotyledons were incubated under continuous illumination at 25° C. for 48 h and the change in fresh weight and chlorophyll content determined.

| Treatment | Change in fresh weight (mg) | % of control | Chlorophyll (μg/cotyledon) a + b | Chlorophyll (mg/g FW) a + b | Chlorophyll a/b |
|---|---|---|---|---|---|
| NAE-10:0 | 11.56 ± 2.16* | 143 | 22.57 | 1.41 | 1.8 |
| NAE-12:0 | 8.53 ± 1.59 | 105 | 23.16 | 1.79 | 2.0 |
| NAE-14:0 | 7.91 ± 1.34 | 98 | 23.41 | 1.90 | 1.8 |
| NAE-16:0 | 12.42 ± 2.26* | 153 | 24.18 | 1.44 | 1.7 |
| NAE-18:0 | 7.75 ± 1.01 | 96 | 22.42 | 1.85 | 1.9 |
| NAE-18:1(Δ9) | 5.78 ± 0.96 | 71 | 20.29 | 1.99 | 2.0 |
| NAE-EH | 7.69 ± 1.16 | 95 | 19.73 | 1.63 | 1.8 |
| NAE-Bz | 7.36 ± 1.00 | 91 | 20.87 | 1.77 | 1.8 |

EXAMPLE 4

Corn root bioassay: It is well established that roots of *Zea mays* produce ethylene when exposed to a variety of stresses (for review, see Morgan, PW and Drew, MC, *Physiologia Plantarum* 100: 620–630, 1997). Mechanical impedance and hypoxia both induce ethylene formation and usually as early as 1 hour after exposure. In response to ethylene treatment, maize roots show decreased expansion and elongation, a high incidence of cell death and the formation of aerenchyma tissue—particularly evident when roots are exposed to hypoxic conditions (Drew, MC et al., *Trends in Plant Science* 5: 123–127, 2000, Morgan and Drew 1997).

Seeds of *Zea mays* L. were sown in flats of Perlite, covered with a layer of vermiculite, and irrigated daily with water and/or 1/10 Hoagland solution. Seedlings were cultivated under continuous illumination at 22–25° C. and used when 7 d old. Seedlings were removed from the Perlite and washed under running tap water. Seedlings were allowed to acclimate in water and/or 1/10 Hoagland solution for several hours before being transferred to Falcon tubes containing the test compounds (all 20 mg/l) prepared in 1/10 Hoagland solution. Seedlings were incubated under continuous light for 24 to 60 hours, the roots excised and the fresh weight determined. Roots were then transferred to gas-tight tubes each containing 200 μl of water. The tubes were sealed and incubated at 26° C. for 1–2 h in darkness before gas samples were drawn from the incubation tubes using a 1 ml syringe and assayed by gas chromatography (Romera, FJ et al. (1999) *Annals of Botany* 83, 51–55).

RESULTS

The results from two independent experiments shown in Tables 4 and 5 indicate that all of the NAEs tested induced ethylene formation. The relative efficacy of the NAEs varies somewhat between the two experiments. NAE-6:0 had the strongest effect in the first experiment and NAE-8:0 had the strongest effect in the second experiment. In other experiments conducted using a different treatment time, some of the NAEs that showed efficacy in Tables 4 and 5 did not increase ethylene production. However, these same experiments showed that other NAEs such as NAE-1, NAE-4:0 and NAE-18:1(Δ9) were effective under the experimental conditions. Accordingly, the optimal conditions for increasing ethylene production for a particular application may vary and a skilled artisan can readily determine the optimal conditions through routine exprimentation.

TABLE 4

Effect of NAEs on ethylene production by maize roots (experiment 1). Seedlings were stood in tubes containing 20 mg/l NAE and incubated under continuous illumination for 72 h. Roots were blotted dry and placed into gas tight tubes, incubated for 2 h, and ethylene analyzed by gas chromatography.

| Treatment | Ethylene nL/g FW/h | % of control |
|---|---|---|
| Control | 590.6 ± 108.8 | 100 |
| NAE-1 | 1034.4 ± 255.3 | 175 |
| NAE-2 | 862.2 ± 101.6 | 146 |
| NAE-6:0 | 1244.0 ± 406.2 | 210 |
| NAE-8:0 | 685.2 ± 211.6 | 116 |
| NAE-10:0 | 734.4 ± 108.1 | 124 |

TABLE 5

Effect of NAEs on ethylene production by maize roots (experiment 2). Seedlings were stood in tubes containing 20 mg/l NAE and incubated under continuous illumination for 36 h. Roots were blotted dry and placed into gas tight tubes, incubated for 2 h in darkness at 24° C. and ethylene analyzed by gas chromatography.

| Treatment | Ethylene pmol/g FW/h | % of control |
|---|---|---|
| Control | 28.79 ± 21.53 | 100 |
| NAE-1 | 45.32 ± 18.98 | 157 |
| NAE-2 | 45.96 ± 12.53 | 160 |
| NAE-6:0 | 40.58 ± 11.85 | 141 |
| NAE-8:0 | 55.46 ± 31.59 | 193 |
| NAE-10:0 | 33.02 ± 9.63 | 115 |

We claim:

1. A method for enhancing fruit ripening comprising the step of treating a fruit or fruit-bearing plant with a composition comprising an N-acylethanolamine (NAE) defined by the following formula: $RCONHCH_2CH_2OH$, wherein R is hydrogen, or a straight, branched, cyclic or polycyclic, saturated or unsaturated $C_1$–$C_{22}$ alkyl group, the composition applied to the fruit or plant in sufficient amount to cause enhanced ripening of the fruit.

2. The method of claim 1, wherein the fruit or fruit-bearing plant is treated with the composition before the fruit is harvested.

3. The method of claim 1, wherein the fruit is treated with the composition after the fruit is harvested.

4. The method of claim 1, wherein treating the fruit or fruit-bearing plant with the composition is accomplished through a method selected from spraying the fruit or fruit-bearing plant with the composition, dipping the fruit or fruit-bearing plant into the composition, or vacuum infiltrating the composition into the fruit.

5. The method of claim 1, wherein the NAE is selected from NAE-1, NAE-2, NAE-4:0, NAE-6:0, NAE-8:0, NAE-10:0, NAE-18:1 (Δ9).

6. The method of claim 1, wherein the NAE concentration in the composition is from about 1 mg/l to about 2,000 mg/l.

7. The method of claim 1, wherein the NAE concentration in the composition is from about 10 mg/l to about 1,000 mg/l.

8. The method of claim 1, wherein the NAE concentration in the composition is from about 20 mg/l to about 500 mg/l.

* * * * *